United States Patent [19]

Kawano

[11] Patent Number: 4,867,739
[45] Date of Patent: Sep. 19, 1989

[54] STERILIZING METHOD

[75] Inventor: Yasuhiro Kawano, Kanagawa, Japan

[73] Assignee: Kawasumi Laboratories Inc., Tokyo, Japan

[21] Appl. No.: 745,658

[22] Filed: Jun. 17, 1985

Related U.S. Application Data

[63] Continuation of Ser. No. 454,475, Dec. 29, 1982, abandoned.

[30] Foreign Application Priority Data

Mar. 26, 1982 [JP] Japan ........................................ 47293

[51] Int. Cl.$^4$ ............................................... A61M 5/00
[52] U.S. Cl. ......................................... 604/4; 604/905
[58] Field of Search ...................................... 604/4–10, 604/264, 247, 250, 905; 128/DIG. 3; 422/44–48, 52; 210/321.2

[56] References Cited

U.S. PATENT DOCUMENTS

| | | | |
|---|---|---|---|
| 2,452,643 | 11/1948 | Fields | 604/905 |
| 3,511,238 | 5/1970 | Von Wrangell | 604/4 |
| 3,811,800 | 5/1974 | Shill | 604/5 |
| 3,960,149 | 6/1976 | Bujan | 604/250 |
| 4,294,247 | 10/1981 | Carter et al. | 604/905 |
| 4,340,049 | 7/1982 | Munsch | 604/905 |
| 4,347,874 | 9/1982 | Sullivan et al. | 604/250 |
| 4,353,368 | 10/1982 | Slovák et al. | 604/5 |

OTHER PUBLICATIONS

Cavanaugh et al., "Hemodialysis Blood Transport System" IBM® Technical Disclosure Bulletin vol. 19 No. 3, 8/1976 (604//4).

Primary Examiner—C. Fred Rosenbaum
Attorney, Agent, or Firm—Michael J. Striker

[57] ABSTRACT

A humors processing device is such as an artificial kidney, artificial liver or others. The device is connected with a humors circulating line which is provided with bags supporting physiological saline solution and with communicating mechanisms at appropriate portions of the same, and the communicating mechanism is ready for opening by finger pressure.

13 Claims, 1 Drawing Sheet

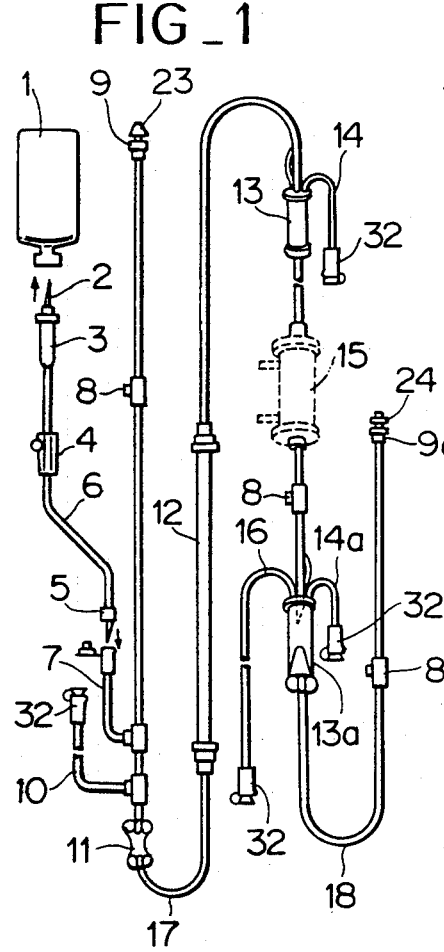
FIG_1
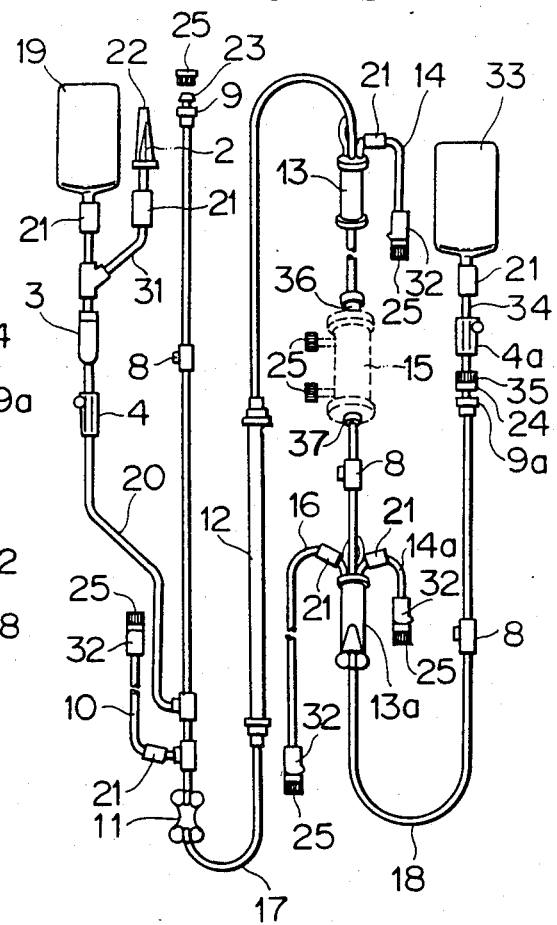
FIG_2
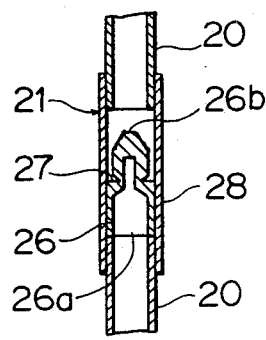
FIG_3
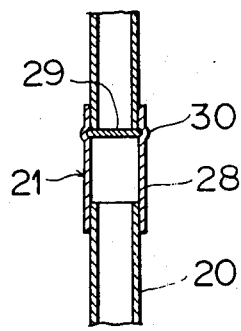
FIG_4

STERILIZING METHOD

This is a continuation of application Ser. No. 454,475 filed Dec. 29, 1982 now abandoned.

BACKGROUND OF THE INVENTION

The present invention relates to a sterilizing method for a blood processing device such as an artificial kidney or the like.

As the blood processing device, there have been artificial kidney, liver, lungs, curing abdominal dropsy processing device, or plasma separator, which serve as substitutions for the organs of the human body. Each of them circulates the blood externally of the human body and removes waste materials in the blood by utilizing a combination of filtrating, dialyzing, absorbing and other processes, or utilizing anyone of them individually.

For these devices, a membrane module or a hemoperfusion cartridge are frequently employed. The former is made by assembling membranes of hollow fibers of from about several hundred to about 10,000 of a cellulose such as cuprammonium rayon or viscose rayon, or a synthetic polymer such as polyvinylalcohol, polymethacryrate, polypropylene or polyacrylonitrile. The latter is made of petroleum-based activated charcoal or plum husk-based activated charcoal.

Said membrane or hemoperfusion cartridge are dealt with by an ethylene oxide gas sterilizing method, a gamma radiation sterilizing method, a formaline sterilizing method, or a steam sterilizing method. However, since the two former methods carry out the sterilization under the dried condition, they will perhaps reduce functions of the membrane. Especially, with respect to the hollow fiber membrane, in case of the dried condition, the blood runs unsmoothly within the hollow fibers, so that air bubbles are removed. Further in the ethylene oxide gas sterilization, residual toxicity after the sterilization is problem. The gamma radiation sterilization modifies or dissolves the membrane, the casing or other parts, and consequently the dissolved substances will elute into the blood. In the formalin sterilization, the formalin per se is harmful to the human body. Therefore, the device should be washed away for a long period of time.

In these circumstances, recently a steam autoclave sterilizing method has been much used. This method has been employed not only in the blood processing device but also in indwelling catherters and the blood circulating line or tube which communicates a patient with the blood processing device. However, in this sterilizing method, the blood processing device and the blood circulating line are sterilized individually, and they should be connected for use. If the blood processing device of the wet condition is used at connection, the liquid leaks from an inlet or an outlet of the device and the device is polluted, and the air will go thereinto.

Since the blood line should be soft and transparent, frequently used is a PVC resin forming agent containing plasticizer such as dioctyl phthalate. However, if the resin which contains the plasticizer contacts an electrolyte such as a physiological saline solution, the plasticizer enters, though only slightly, the electrolyte. If the sterilization is carried out under the condition of filling the physiologocal saline solution, the filled solution is discharged before use of the circulating line, and it is necessary to wash the line with a new physiological saline solution and take out the air from the line. This is known as a priming.

The priming is undertaken, as shown in FIG. 1, by connecting an inlet circulating line 17 and an outlet circulating line 18 to the blood processor 15, connecting a priming set 6 having a clamp 4, a drip chamber 3 and others to a priming line 7 which branches from the main tube of the inlet line 17, piercing an introducing needle 2 at an end point of the priming set 6 into a mouth of a bottle 1 supporting the physiological saline solution, and running the solution within the bottle into the inlet line 17, the outlet line 18 and the blood processor 15.

However, in such conventional methods, it is necessary to take trouble of disinfecting a needle piercing portion of a rubber plug in the bottle mouth, when the connector 5 is stiffly mounted at the end of the priming line 7 or the needle 2 is pierced into the mouth of the bottle. In addition, if the introducing needle is plastic, large force is required. Further, it is necessary to clamp luer connectors 32 by means of many forceps for preventing leakage of the physiological saline solution. The prior art is troublesome in preparation requiring much processes and therefore it is unhygienic.

In addition, when the priming is opened, the waste liquid is discharged from the outlet 24 of the outlet line 18, and at this time the outlet 24 is held with an adhesive tape to an edge of a vessel such as a bucket. This manner makes the outlet 24 touch the vessel, or directly exposes it in the air. This is unsanitary. Further, it is troublesome to support the outlet 24 to the vessel with the adhesive tape.

The present invention has been devised to remove disadvantages involved in the prior art.

An object of the invention is to enable to carry out the steam autoclave sterilization under condition of communicating all of the processing device, the inlet line, the outlet line and others, whereby the connecting operation during use is no longer necessary, so that the cost for the sterilization is lowered.

Another object of the invention is to provide a blood processing device where preparation for the priming is performed easily and hygienically.

A further object of the invention is to deal with the waste solution in an easy and hygienic manner.

Another object of the invention is to provide a blood processing device which is convenient to an urgent case or home dialysis which has been recently popular.

Other objects will be apparent from explanation of the invention in reference to the attached drawing and the appended claims.

BRIEF DESCRIPTION OF THE DRAWING

FIG. 1 is an outlined view of a conventional humors processing device,

FIG. 2 is an outlined view showing a whole device according to the invention,

FIGS. 3 and 4 are cross sectional views of communicating mechanisms according to the invention.

DETAILED DESCRIPTION OF PREFERRED EMBODIMENT OF THE INVENTION

In FIG. 2, the numeral 15 shows a blood processor. The device comprises about 10,000 of membranes of hollow fibers made of cellulose or synthetic polymer, and purifies the blood by filtrating or dialyzing while the blood passes through the hollow fibers. The processor 15 has a blood inlet 36 and a blood outlet 37 at its ends, and they are connected to a blood inlet line 17 and a blood outlet line 18, which compose a blood line.

The lines 17, 18 are in general made of flexible synthetic resin, say, PVC. A main tube of the line 17 is provided with an air trap 13, a pump tube 12 and a negative pressure monitor 11. A main tube of the line 18 is also provided with an air trap 13a. The negative pressure monitor 11 is to notice abnormal pressure in the inlet line 17.

The air traps 13, 13a serve to remove the air in the blood, and are connected to level adjustment lines 14, 14a which keep constant surfaces of the blood in the air traps. The air trap 13a of the blood outlet line 18 is connected to a pressure monitor line 16 which observes the pressure of the blood under processing.

A blood inlet 23 and a blood outlet 24 are equipped with shunt adapters 9, 9a, respectively. The inlet line 17 and the outlet line 18 are provided at appropriate portions with injection sites 8 for injecting liquid medicine or sampling the blood. The inlet line 17 has a heparin line 10 which branches from the main tube for injecting anticoagulant solution. On the other hand the inlet line 17 branches, from the main tube, a communicating tube 20 to be a priming line which is connected at its end portion with a bag 19 of soft synthetic resin filled with the physiological saline solution. The communicating tube 20 is positioned with a clamp 4 which adjusts the flow amount of the physiological saline solution and a drip chamber 3 which observes its flow amount. Further the communicating tube 20 branches a preparatory line 31 from a higher portion than the drip chamber 3, which is to connect a bag or bottle supporting the physiological saline solution for a case of lacking the solution, and has an introducing needle 2 at its end portion with a protecting cap 22.

The bag may be directly connected to the tube 20, but in the present embodiment, this connection is made via a communicating portion 21 which is easily opened by the finger pressure.

FIGS. 3 and 4 illustrate examples of the above mentioned communicating portions. In FIG. 3, the tube 20 is mounted at its middle part with a flexible communicating tube 28 which has a larger diameter than that of the tube 20, and the tube 28 is supported with a communicating tube 26 therein. The tube 26 is made of hard synthetic resin and has an outer diameter almost equal to an inner diameter of the communicating tube 28. With respect to the communicating tube 26, a lower end portion 26a opens and an upper end portion is closed with a head 26b whose diameter is smaller than that of the tube 28 but larger than an inner diameter of the tube 20, and the head 26b is formed with a thin film portion 27 at its lower part. If the tube 28 is pressed by the fingers from an external side, the head is broken at the thin film 27 to communicate with the tube 20. Since the head 26b is crashed, the separated head 26b does not perfectly close the communicating tube 20.

In FIG. 4 the communicating tube 28 is adapted under pressure with a circular communicating piece 29 which is larger than the tube 28 in diameter, so that the tube 28 holds the piece 29 by a holding portion 30 which is made by said adaption, and the piece 30 is laid by the finger pressure from the external side.

The communicating tubes 21 having such mechanisms are also provided at the preparatory line 31, and further on the heparin line 10, the level adjusting lines 14, 14a and the pressure monitoring line 16. In a line having a protamine line, said communicating mechanisms may be provided nearly a branching portion of the protaline line.

On the other hand, in the invention, an adapter 9a of the humors outlet line 18 is connected with a waste liquid bag 13 which is made of soft synthetic resin as the bag 19. In the present embodiment, a communicating portion 21 which has the same mechanism as said above, is positioned on a tube 34 extending from the waste liquid bag 33 and a clamp 4a is equipped thereon, and a connector 35 is detachably connected with an adapter 9a.

Sealings are made by means of water tight-caps or sealing members 25 on mouths of the luer connectors 32 at the ends of the branches lines 10, 14, 14a, 16, the shunt adapters 9,9a and the blood processor 15, so that interiors of the inlet line 17, the outlet line 18 and the processing device 15 are perfectly interrupted externally.

Under this condition, the lines 17, 18 and the blood processor 15 are filled with harmless liquid, for example, the physiological saline solution or distilled water. The solution is charged thereinto by effecting pressure from the adapter 9 of the inlet line 17, or by effecting negative pressure from the outlet 24 of the outlet line 18.

The blood processing device is charged with the harmless liquid, and carried out with the autoclave sterilization in the saturated steam of 121° C.×20 min decided by Japanese Pharmacopeia, under the condition that each of said mouths is sealed with sealing member 25, and the processor 15, the inlet line 17, the outlet line 18 and the waste liquid bag 33 are connected. Accordingly, raw materials for setting up the blood processing device should have durability enough to temperatures of said autoclave sterilization, and property difficult to deform. For example polycarbonate is used for the outer body of the processor 15, polycarbonate or polypropylene are used for the sealing member 25, and PVC, silicone or polyurethane resin are used for the blood circulating lines 17, 18. For other parts, such property is preferable which is heat-resistant and antideform.

A further reference will be made to the priming operation. There are, at determined positions, the blood lines 17, 18, the processor 15 and the bag 19. The sealing member 25 is taken off from the blood introducing mouth 23 of the inlet line 17, and the opened mouth is positioned at the lower place, and after the liquid in the inlet line 17 is discharged, the portion 21 at the end of the communicating tube 20 is communicated by the finger pressure to introduce the physiological saline solution from the bag 19 thereinto.

Subsequently, a portion 21 near to the waste solution bag 33 of the tube 34 is communicated by the finger pressure, and a liquid feed pump (not shown) is worked moderately and squeezes a pump 12 thereby to issue out the liquid in the inlet line 17, the processor 15 and the outlet line 18 from the outlet 24, and while the physiological saline solution is substituted, the air introduced by the sterilization is removed.

Thus, the physiological saline solution is let flow until the air is completely removed, and if the prepared physiological saline solution were not enough, the introducing needle 2 would be pierced into the solution bottle or bag and the communicating portion 21 on the preparatory line 31 is crashed and supplement the solution.

The waste solution is stored in the bag 33 through the blood exhausting outlet 24. After completion of the priming, the clamp 4a is closed and the connector 35 is removed from the adapter 9, and the waste solution is discharged.

According to the present invention having been mentioned above, lots of merits are brought about, that is, (1) since it is possible to undertake the autoclave sterilization under the condition of combining all of the processing device, blood circulating lines and bags, the combination is not required during use, and the filled solution is not leaked, and the cost of processing sterilization is lowered.

(2) it is no longer necessary to connect the priming set as conventionally and clamp it by means of the forceps, and since the communicating portion is opened by the finger pressure if occasions demand, the priming preparation is made under the perfectly sealing condition, and the waste solution can be dealt with easily and hygienically, and (3) it is used at the urgent case or the home dialysis which has been recently popular.

This invention may be of course applied to the blood processing device such as the artificial kidney, liver, lungs, abdominal dropsy processing device, or plasma separator.

The actual embodiments of the structure are not limited to those of the blood inlet and outlet lines as illustrated, but vary in accordance with blood processing devices to be used.

What is claimed is:

1. A sterilization method for a blood processing device which circulates blood externally of a human body and removes waste material from the blood, the method comprising the steps of: providing a blood processor having an inlet and an outlet; connecting a blood inlet line and a blood outlet line to said blood processor inlet and outlet, respectively; connecting a branched tube to said blood inlet line; filling both said blood inlet line and said blood outlet line and also said blood processor and said branched tube with a liquid harmless to the human body; subjecting said filled blood inlet line and blood outlet line and blood processor to an autoclave sterilization in a saturated steam so that said liquid in said inlet and outlet line and said blood processor is heated whereby said inlet and outlet line and said blood processor are sterilized; connecting a bag filled with physiological saline solution to said branched tube using a finger pressure openable communicating mechanism for establishing and interrupting communication between said bag and said branched tube; connecting a waste bag to said blood outlet using another communicating mechanism; and causing the saline solution to flow from said bag filled with solution by opening said communicating mechanism, thereby forcing the liquid in said blood inlet line, said blood processor and said blood outlet line into said waste bag.

2. A method as defined in claim 1; and further comprising the step of connecting a preparatory tube having an introducing needle at its one end, to said branched tube at its other end.

3. A method as defined in claim 2, wherein said preparatory tube connecting step includes connecting said preparatory tube to said branched tube by a communicating mechanism openable by finger pressure for establishing and interrupting communication.

4. A method as defined in claim 1; and further comprising the step of connecting a plurality of branched line tubes to said blood inlet line and said blood outlet line by communicating mechanisms openable by finger pressure.

5. A method as defined in claim 4, wherein said step of connecting a plurality of branched line tubes includes connecting a heparin injection line to said blood inlet line.

6. A method as defined in claim 4, wherein said step of connecting a plurality of branched line tubes includes connecting a level adjusting line.

7. A method as defined in claim 4, wherein said step of connecting a plurality of branched line tubes includes connecting a pressure monitoring line to said blood outlet line.

8. A method as defined in claim 4, wherein said step of connecting a plurality of branched line tubes includes connecting a protamine line.

9. A method as defined in claim 1, wherein said waste bag connecting step and said bag connecting step include connecting with a communicating mechanism having a flexible communicating tube and a tube of hard property placed within said flexible communicating tube, said hard tube being formed with a thin film portion.

10. A method as defined in claim 1, wherein said waste bag connecting step and said bag connecting step include connecting with a communicating mechanism having a flexible communicating tube and a communicating piece adapted under pressure for interrupting a passage within said communicating tube.

11. A method as defined in claim 1, wherein said saline filled bag connecting step includes connecting a bag made of a soft synthetic resin.

12. A method as defined in claim 1, wherein said waste solution bag connecting step includes connecting a waste solution bag made of a soft synthetic resin.

13. A method as defined in claim 1, wherein said waste solution bag connecting step includes detachably connecting said waste solution bag to said blood outlet line.

* * * * *